United States Patent
Piercey et al.

(10) Patent No.: US 11,858,902 B2
(45) Date of Patent: Jan. 2, 2024

(54) HIGH-PERFORMING METAL-FREE PRIMARY EXPLOSIVE

(71) Applicant: Purdue Research Foundation, West Lafayette, IN (US)

(72) Inventors: Davin Glenn Piercey, Lafayette, IN (US); Dominique Wozniak, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 414 days.

(21) Appl. No.: 17/221,866

(22) Filed: Apr. 5, 2021

(65) Prior Publication Data

US 2022/0048870 A1 Feb. 17, 2022

Related U.S. Application Data

(60) Provisional application No. 63/038,158, filed on Jun. 12, 2020.

(51) Int. Cl.
*C07D 249/04* (2006.01)
*C06B 25/00* (2006.01)

(52) U.S. Cl.
CPC ............ *C07D 249/04* (2013.01); *C06B 25/00* (2013.01)

(58) Field of Classification Search
CPC .. C07D 249/00; C07D 249/04; C07D 249/08; A61K 31/41
See application file for complete search history.

(56) References Cited

U.S. PATENT DOCUMENTS 5,889,161 A 3/1999 Bottaro et al.

OTHER PUBLICATIONS

Klapötke, Thomas M. et al. "Amination of energetic anions: high-performing energetic materials." Dalton transactions 41 31 (2012): 9451-9 . (Year: 2012).*
Qu, Y., & Babailov, S. P. (2018). Azo-linked high-nitrogen energetic materials. Journal of Materials Chemistry. A, Materials for Energy and Sustainability, 6(5), 1915-1940. (Year: 2018).*

* cited by examiner

*Primary Examiner* — Theodore R. Howell
*Assistant Examiner* — Pierre P Eleniste
(74) *Attorney, Agent, or Firm* — Purdue Research Foundation

(57) ABSTRACT

The present disclosure relates to a novel compound suitable for a metal-free primary explosive, and the method of making and using the novel compound. The novel compound can undergo a deflagration to detonation transition (DDT) to initiate detonation of a larger body of secondary explosive. The compound has a structure of Formula I:

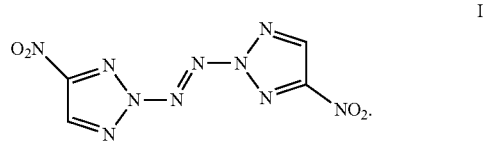

3 Claims, 2 Drawing Sheets

HIGH-PERFORMING METAL-FREE PRIMARY EXPLOSIVE

CROSS-REFERENCE TO RELATED APPLICATION

The present Application claims the priority benefit of U.S. Provisional Application No. 63/038,158, filed Jun. 12, 2020, and the content of which is hereby incorporated by reference in its entirety.

GOVERNMENT RIGHTS

This invention was made with government support under Award No. W911NF-18-1-0463 awarded by the Army Research Office. The government has certain rights in the invention.

TECHNICAL FIELD

The present disclosure relates to a novel compound suitable for a high-performance metal-free primary explosive, and the method of making and using the novel compound. The novel compound can undergo a deflagration to detonation transition (DDT) to initiate detonation of a larger body of secondary explosive.

BACKGROUND

This section introduces aspects that may help facilitate a better understanding of the disclosure. Accordingly, these statements are to be read in this light and are not to be understood as admissions about what is or is not prior art.

Energetic materials find wide use in both military and industrial settings. Currently there is a large thrust in the development of high-energy-density materials (HEDMs) that exhibit high performance while maintaining a high level of safety during use and transportation. In pursuit of these materials it is often observed that with increasing energy content there is an accompanying decrease in the stability of the compound to physical stimuli.

Within the field of energetic materials there is a specific push for metal-free, environmentally friendly primary explosives that possess high energy density and still retain a level of stability that allows for their utilization. The requirements for useful primary explosives include thermal stability of at least 180° C. while also being able to undergo a deflagration to detonation transition (DDT) with enough energy to initiate detonation of a larger body of secondary explosive such as 1,3,5-Trinitro-1,3,5-triazinane (RDX). Currently, the available metal-free primary explosives available such as 6-Diazo-2,4-dinitrophenol (DDNP), triacetone triperoxide (TATP), and cyanuric triazide (CTA) are all limited by either their low thermal stabilities low detonation performances or excessive sensitivity.

One method of creating such materials is utilizing the high heat of formation inherent to high-nitrogen materials. Recent studies have showed that by increasing the number of nitrogens contained in a compound, the higher the energy content and sensitivity become. This is especially true of high-nitrogen compounds which have extended chains of several nitrogen atoms in their structure. Unfortunately, as seen with other HEDMs, there seems to be an inverse relationship between detonation performance and stability.

For example 1,1'-azobis-1,2,3-triazole (FIG. 1) has an eight-nitrogen chain and possesses a good thermal stability of 193.8° C., however it is too mechanically insensitive (PETN-like) and does not undergo a DDT in small quantities, precluding its use as a primary explosive. 1,1'-azobis (tetrazole) (FIG. 1) with its ten-nitrogen chain represents the other extreme where its extreme sensitivity to mechanical stimuli and low decomposition temperature of 80° C., renders it impossible for adoption as a primary explosive; it explodes when touched. 2,2'-azobis(5-nitrotetrazole) also extremely easily detonates, while possessing an eight-nitrogen chain.

Therefore, novel compounds that can undergo a deflagration to detonation transition (DDT) to initiate detonation of a larger body of another secondary explosive are still needed.

SUMMARY

The present disclosure relates to a novel compound suitable for a high-performance metal-free primary explosive, and the method of making and using the novel compound. The novel compound can undergo a deflagration to detonation transition (DDT) to initiate detonation of a larger body of secondary explosive.

In one embodiment, the present disclosure provides a compound of Formula I:

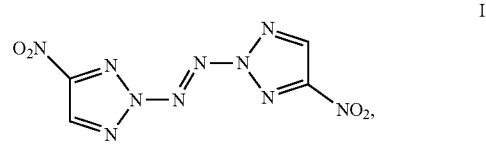 [SMILES: O=[N+]([O-])c1cnn(/N=N/n2ncc([N+](=O)[O-])n2)n1]

I or a stereoisomer thereof.

In another embodiment, the present disclosure provides a method of using the compound of Formula I as a metal-free primary explosive.

DETAILED DESCRIPTION

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In one embodiment, the present disclosure provides a compound of Formula I:

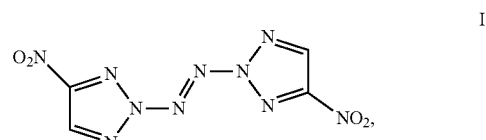

I or a stereoisomer thereof.

In one embodiment, the present disclosure provides a composition, wherein the composition comprises the compound of Formula I.

In one embodiment regarding the compound of Formula I, wherein the compound may comprise E and/or Z stereoisomer.

In one embodiment, the present disclosure provides a method of using the compound of Formula I, wherein the compound is used as a metal-free primary explosive.

In one embodiment regarding the method of using the compound of Formula I, wherein the compound of claim 1 has a thermal stability up to 227° C. and can undergo a deflagration to detonation transition (DDT) to initiate detonation of a larger body of secondary explosive.

Figure 1:
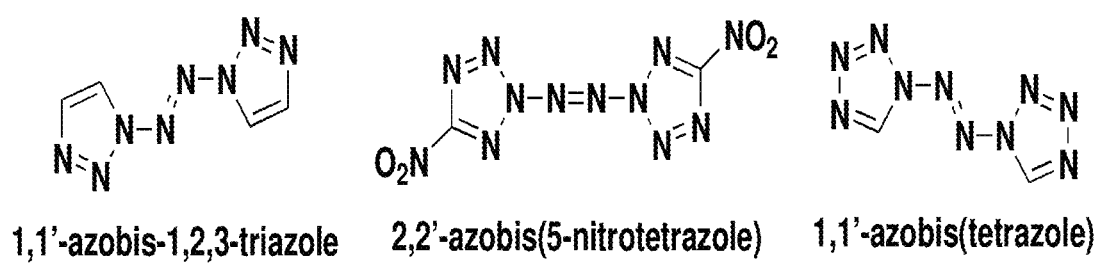
FIG. 1 illustrates energetic compounds containing catenated nitrogen chains.

The present disclosure was influenced by the sensitivity issues represented by azo-coupled compounds such as compounds illustrated in FIG. 1, with 1,1'-azobis(tetrazole) being able to undergo a DDT but too sensitive, and 1,1-azobis-1,2,3-triazole being too stable and not undergoing a DDT, precluding use. The present disclosure provides the study that examined the azo-coupling of 2-amino-4-nitro-1,2,3-triazole 1 and 1-amino-4-nitro-1,2,3-triazole 2 (Scheme 1). These compounds are intermediates between the insensitive 1,1'azobis-1,2,3-triazole and 1,1'-azobis(tetrazole) and had a potential to possess properties that would be ideal in a metal-free primary explosive: being sensitive enough to undergo a DDT, however also being thermally and mechanically stable.

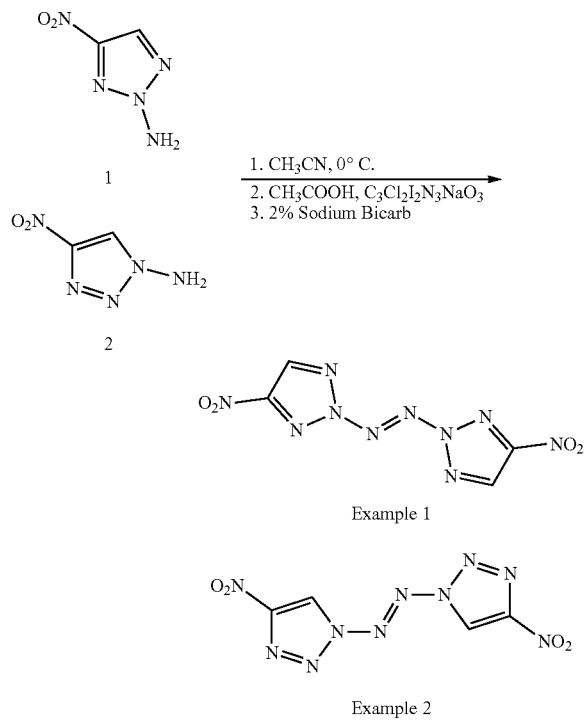

Precursor compounds 1 and 2 were synthesized according to literature methods. (See Wozniak, D. R. et al., Sensitive Energetics from the N-Amination of 4-Nitro-1,2,3-Triazole, *ChemistryOpen* 2020, (9), 1-7, doi[dot]org/10[dot]1002/open[dot]202000053). In previous studies, there was success in procuring catenated nitrogen chains through coupling of N—$NH_2$ bonds with sodium dichloroisocyanurate; this same methodology was applied in this disclosure. The precursor compounds 1 and 2 were reacted separately in acetonitrile at 0° C. with an aqueous acidic solution of sodium dischloroisocyanurate (Scheme 1). The reactions yielded pure Example 1 (1,2-bis(4-nitro-2H-1,2,3-triazol-2-yl)diazene; or 2,2'-azobis(4-nitro-1,2,3-triazole)) and Example 2 (1,2-bis(4-nitro-1H-1,2,3-triazol-1-yl)diazene; or 1,1'-azobis(4-nitro-1,2,3-triazole)) in 71% and 61% yields respectively. No further purification was necessary. $^1H$ and $^{13}C$ NMR spectra were collected for both products. Example 1 and Example 2 had proton peaks present at 9.36 ppm and 10.10 ppm respectively. Example 1 carbon peaks were present at 155.12 ppm, 135.53 ppm. Example 2 carbon peaks were present at 153.02 ppm 129.60 ppm. When comparing the NMR spectra of precursor 1 to Example 1, it was observed that the C—H carbon shifts from 8.53 ppm in precursor compound 1. Both carbon peaks shifted downfield from 149.9 ppm and 129.83 ppm seen in the parent compounds.

Figure 2:
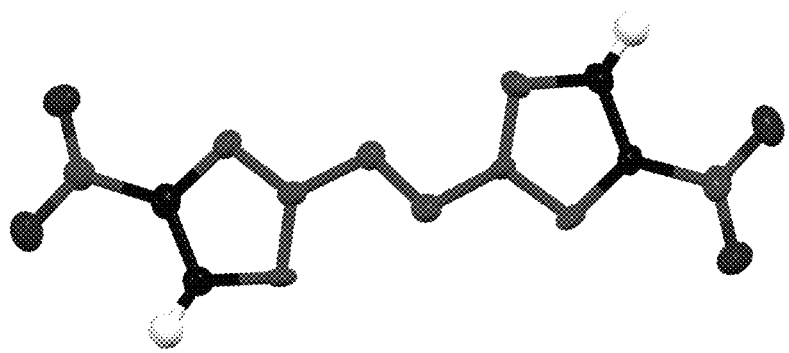
FIG. 2 illustrates OTREP plot of Example 1.
Figure 3:
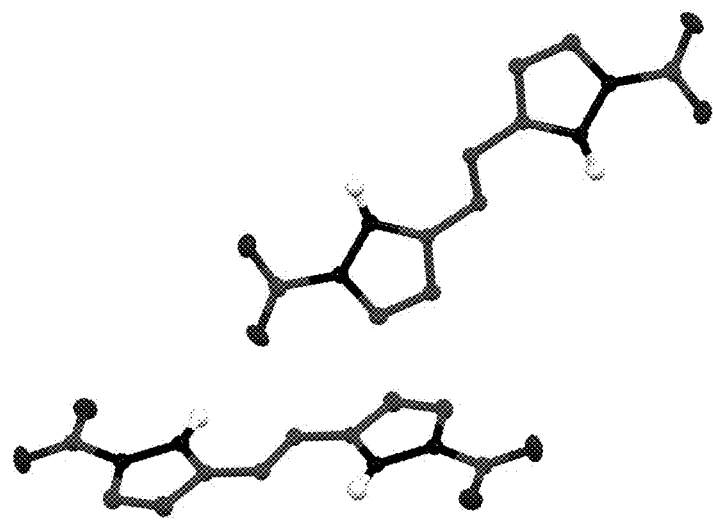
FIG. 3 illustrates OTREP plot of Example 2.

Colorless crystals of Example 1 and Example 2 suitable for x-ray crystallographic analysis were obtained from slow evaporation from acetone over several days at room temperature (FIG. 2 and FIG. 3). Both products crystalize in orthorhombic crystal systems with high densities of 1.840 g $cm^{-3}$ and 1.818 g $cm^{-3}$ respectively. The length azo double bond Example 1 is 1.251 Å, which closely matches that of the $N_8$ compound mentioned previously. The azo double bonds in Example 2 are slightly shorter with lengths of 1.244 Å and 1.246 Å.

Example 2 has a calculated heat of formation of 866.4 kJ $mol^{-1}$, and an impressive calculated detonation velocity of 9014 m $s^{-1}$. It was the more sensitive of the two isomers, with impact sensitivity of <1 J and friction sensitivity of <5 N. Example 1 has a heat of formation of 841.4 kJ $mol^{-1}$ but with its higher density was calculated to have a detonation velocity of 9068 m $s^{-1}$. It is slightly more stable against mechanical stimuli compared to Example 2 with an impact sensitivity between 4.0-4.5 J and friction sensitivity between 36-40 N. This makes it a material with a detonation velocity approaching that of HMX (9193 m $s^{-1}$) while possessing sensitivity to classify it as a primary explosive.

Figure 4:
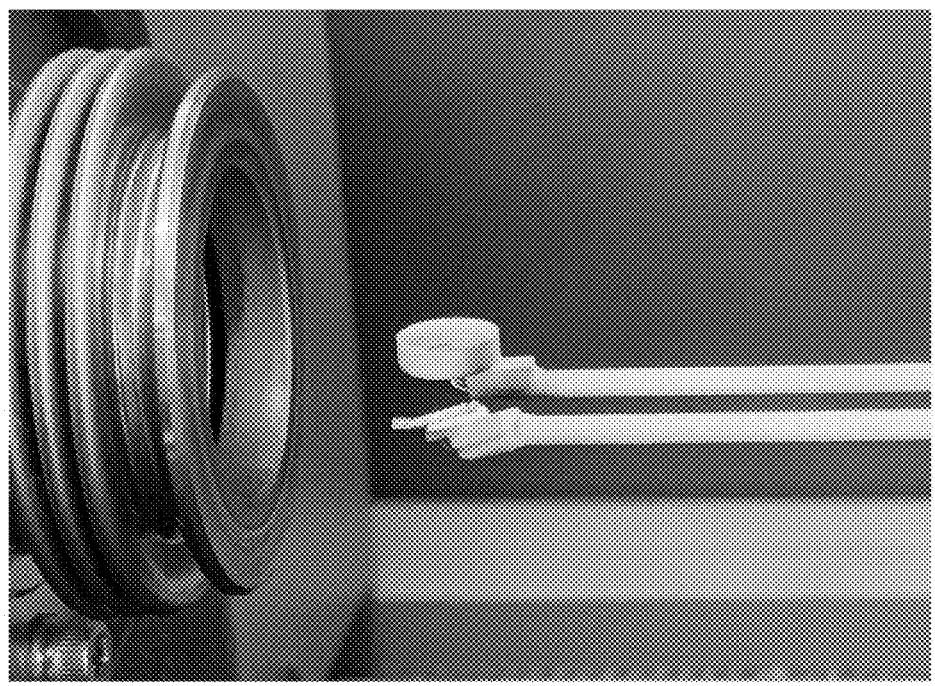
FIG. 4 illustrates damage sustained to DSC sample arm after 0.87 mg of Example 2 detonated at 160° C. The front arm should look like the reverse.

Besides the slight differences in detonation performances and stability against mechanical stimuli, the differences in thermal stability of Example 1 and Example 2 is rather impressive. Example 2 is stable up to 160° C. where it detonates with enough force to decimate the aluminum pan, sample arm, and portions of the reference arm of the DSC/TGA apparatus (FIG. 4). Due to its low thermal stability, Example 2, while powerful, is not a good candidate as a primary explosive. However, Example 1 is thermally stable up to an impressive 227° C. This high thermal stability makes this material an attractive candidate as a new metal-free primary explosive. It is quite surprise to find out that, although both Example 1 and Example 2 have the same number of nitrogen atoms, the more symmetric orientation of triazole nitrogen atoms to the azo group appears to make Example 1 unexpectedly suitable for a primary explosive. The combination of eight nitrogen atoms and the more symmetric orientation of Example 1 clearly has played some unexpected role and has made Example 1 unexpectedly suitable for a primary explosive.

In order to be used as a primary explosive, energetic materials must be able to undergo a DDT. To test this, very small amounts of Example 1 and Example 2 were placed on the tip of a metal spatula and held to a blow-torch. In open air, Example 2 decomposes producing a yellow flame and sharp snap. Example 1 only produces a yellow flame and hissing noise in open air, however with slight confinement such as a single layer of aluminum foil, it produces a loud snapping sound when ignited. This indicates that in sufficiently confined spaces, Example 1 can undergo a DTT and is a viable candidate as a primary explosive.

In conclusion, this disclosure provides the synthesis and characterization of two new energetic azo compounds, Example 1 and Example 2. Due to the sensitivity and high thermal stability of Example 1, combined with its excellent detonation velocity and ability to undergo a DDT, this compound is a promising candidate for use as a metal-free primary explosive. To the best of our knowledge, it possesses the most appropriate properties to function in this role where its high thermal stability, reasonable mechanical stability, and ability to undergo a DDT in small amounts make it more suitable than currently known metal-free primary explosives.

Those skilled in the art will recognize that numerous modifications can be made to the specific implementations described above. The implementations should not be limited to the particular limitations described. Other implementations may be possible.

We claim:

1. A compound of Formula I:

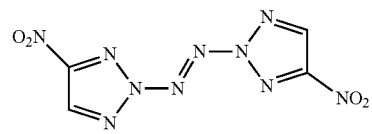

I or a stereoisomer thereof.

2. A composition, wherein the composition comprises the compound of claim 1.

3. A method of using the compound of claim 1, which method comprises deflagrating the compound to detonation transition (DDT) to initiate detonation of a larger body of secondary explosive.

* * * * *